United States Patent [19]

Lee et al.

[11] Patent Number: 4,742,148
[45] Date of Patent: May 3, 1988

[54] MODIFIED IMIDAZOLE LATENT EPOXY RESIN CATALYSTS AND SYSTEMS COMPRISING THEM

[75] Inventors: Frank W. Lee, Dublin; Kenneth S. Baron, San Ramon, both of Calif.

[73] Assignee: Hexcel Corporation, San Francisco, Calif.

[21] Appl. No.: 39,175

[22] Filed: Apr. 17, 1987

[51] Int. Cl.[4] ............................................. C08G 59/50
[52] U.S. Cl. .................................... 528/117; 528/407; 528/96; 548/337
[58] Field of Search .......................... 528/117, 407, 96; 548/337

[56] References Cited

U.S. PATENT DOCUMENTS

| | | | |
|---|---|---|---|
| 3,962,184 | 6/1976 | Notomi et al. | 528/220 X |
| 4,335,228 | 6/1982 | Beitchman et al. | 528/117 X |
| 4,558,115 | 12/1985 | Mefner | 528/117 X |
| 4,559,398 | 12/1985 | Tesch et al. | 528/117 X |
| 4,587,311 | 5/1986 | Schmid et al. | 528/117 X |

*Primary Examiner*—Earl Nielsen
*Attorney, Agent, or Firm*—Oblon, Fisher, Spivak, McClelland & Maier

[57] ABSTRACT

A latent catalyst for epoxy resin systems is produced by the reaction between an aromatic dicyanate and imidazoles. The catalyst provides good curability, excellent mechanical properties, and remarkably extended shelf life. It also allows curing at room temperature.

9 Claims, No Drawings

MODIFIED IMIDAZOLE LATENT EPOXY RESIN CATALYSTS AND SYSTEMS COMPRISING THEM

BACKGROUND OF THE INVENTION

1. Field of the Invention

This invention pertains to one-shot or one-component epoxy resin systems and latent catalysts therefor. More particularly, it addresses modified imidazoles useful as latent catalysts in such systems.

2. Background of the Prior Art

Increasing attention, particularly in the composites field, has been concentrated on "one-shot" or "one-component" epoxy resin systems, as having excellent mechanical properties for a variety of applications, including prepregs, laminates, bonding adhesives, coatings, finishes, tooling resins, pultrusion, etc., without requiring sophistication on the part of the user, or sophisticated apparatus.

Unfortunately, these systems, in which a latent catalyst is dispersed in the unpolymerized or uncured resin, inactive at room temperatures or lower, have been plagued by several problems. Chief amongst these problems is the limited shelf-life of these single package systems. They tend to cure, or polymerize, rapidly and prematurely, in a matter of days, up to a week or two. Of course, this puts extreme demands on inventory, and price, and similarly, makes the material difficult to work with on a large project, which takes a substantial amount of time to bring to completion.

Another problem encountered is the heat levels, or prolonged exposure to high heat levels, necessary to cure these systems.

As an example, imidazole, and imidazole derivatives have been used as latent catalysts giving polymeric materials that cure quickly, and have excellent mechanical characteristics. However, these have a very short shelf life, 1-2 days at most at ambient conditions. Any processing delays encountered may result in a loss of half the resin or more, as a result of its short shelf life.

There have been prior art attempts to overcome these problems. Thus, U.S. Pat. No. 4,335,228, describes isocyanate blocked imidazoles/imidazolines for use as latent catalysts in epoxy resin systems. However, such catalyst must be used with epoxy resins that have a melting temperature of 60° C. or above. They also require cure temperatures of 250-400° F.

European patent application No. 0024119 describes a one-package system using a succinic acid salt of a phenylisocyanate-modified imidazole as a latent catalyst. However, when combined with an epoxy resin prepared from polyglycidyl ether, the resulting product was found to have only 2-3 days shelf life at room temperature.

Of course, other catalysts, such as dicyandiamide, are known, having excellent shelf-life. However, the curing temperatures of these, 350° F. and above, are too high for many preferred applications. Of course, curing may be accelerated by addition of various salts of amines, and ureas. However, these additives dramatically reduce the shelf-life of the resin system, and adversely affect the properties of the resulting cured product.

Accordingly, it remains a goal of the art to provide a one-package epoxy resin system, comprising a latent catalyst, which results in good mechanical properties in the cured product, while exhibiting an extended shelf-life.

SUMMARY OF THE INVENTION

It is one object of this invention to provide a latent catalyst for epoxy resin systems, and systems comprising that catalyst, that exhibit excellent shelflife, on the order of weeks or greater.

It is another object of this invention to provide an epoxy resin latent catalyst, and systems comprising that catalyst, which gives satisfactory mechanical properties upon curing.

It is yet a further object of this invention to provide a one-shot epoxy resin system, comprising a latent catalyst, which is cured easily, and at relatively low temperatures.

These and other objects of the invention made clear below are achieved by use of a latent catalyst that is the reaction product of a dicyanate and imidazole. The latent catalyst has the structural formula (I) set forth below.

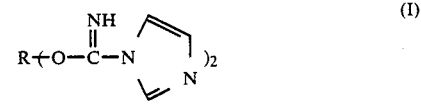

The central R group can be any aryl radical, particularly including phenyl, naphthyl and diphenyl and dinaphthyl combinations. R is not limited, save for its aromatic nature, and solubility considerations, where the catalyst is to be dispersed in a liquid system.

1, 2 or 3 of the carbon positions may be substituted, as desired. Such substitution may have a further impact on solubility. The substituent(s) may be the same or different where plural and can be hydrogen, alkyl or aryl of $C_{1-12}$, halos, nitros, etc. Representative species include Imidazole, 2-ethyl imidazole, 2-ethyl-4-methylimidazole, 2-phenylimidazol, 4-nitroimidazole, 2-methyl-4(5)-nitroimidazole, 2-isopropylimidazole, 2-isopropyl-4(5)-nitroimidazole, 4-methylimidazole, 2-chloro-imidazole, 4-methyl-5-imidazolcarbon squareethylester, Benzimidazol.

Conventional epoxy resin systems using this latent catalyst, e.g., systems employing derivatives of polyglycidyl ether, have mechanical properties, when cured, that equal or excel those of conventional imidazole systems, and simultaneously exhibit a dramatically increased shelf life, of 10 days up to a few months, while subject to being cured at temperatures as low as room temperature, and having extended "out time" at these low temperatures.

DETAILED DESCRIPTION OF THE INVENTION

Applicants' invention resides in the discovery that the reaction product of an aromatic dicyanate and imidazoles leads to a latent catalyst which gives excellent mechanical properties, when cured, requires minimal exposure to relatively low heat for curing, and most importantly, exhibits a significantly extended shelf life.

The catalyst is defined by the formula I set forth below:

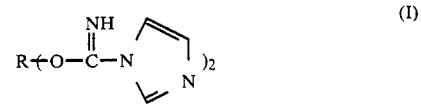

Central group R can be virtually any aromatic which is not unduly reactive (i.e., reacts by itself) and preserves any necessary solubility characteristics. In particular, greater insolubility in the resin generally leads to longer out times. Examples of R groups acceptable include
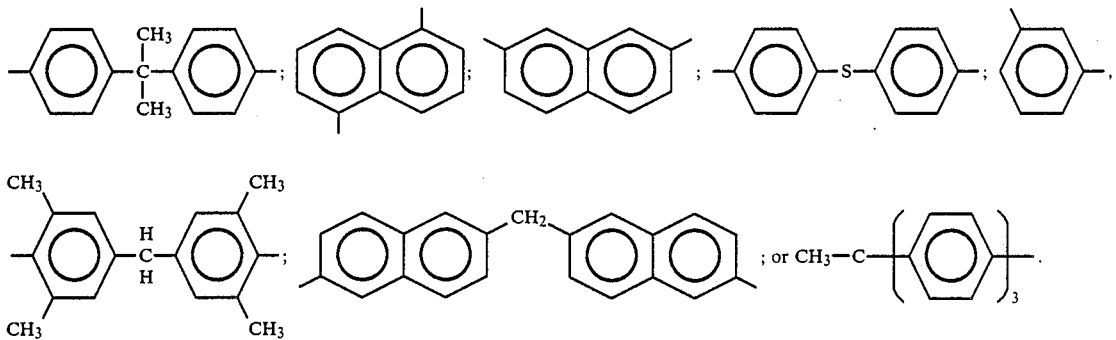
Aromatic cyanates which can be used include:
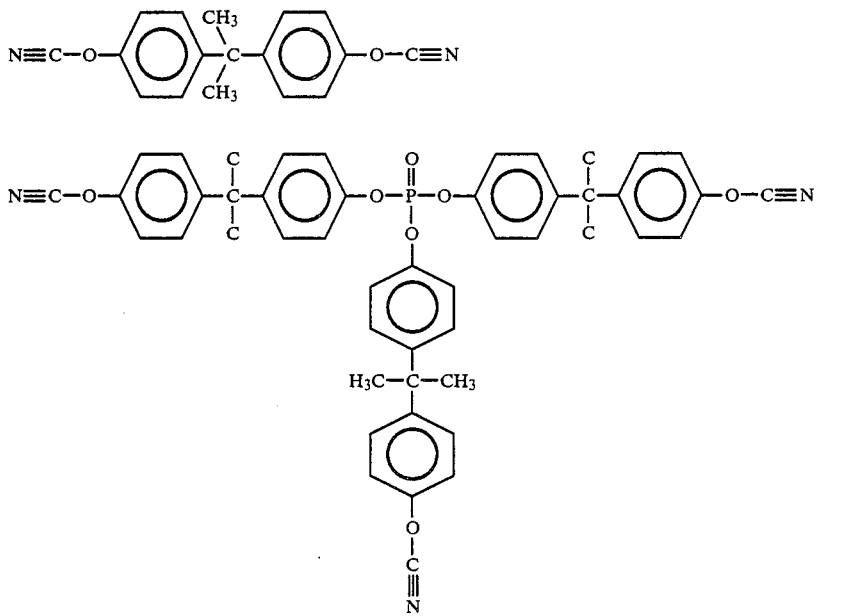
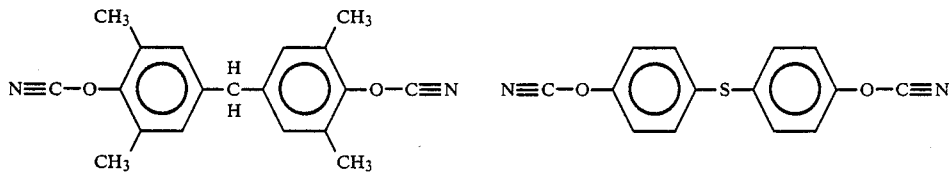
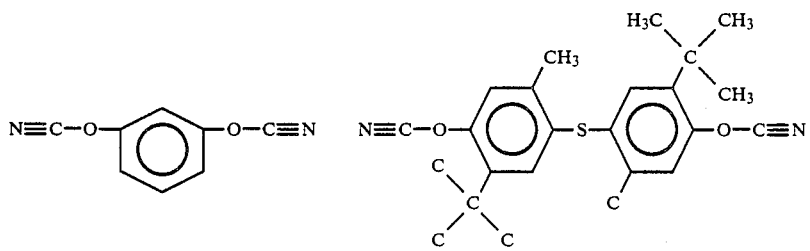

-continued

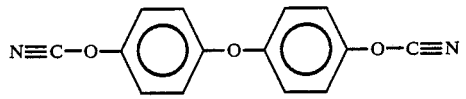
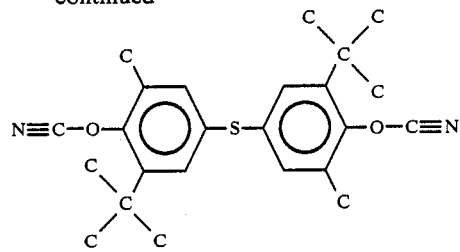

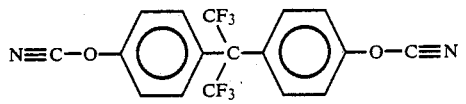

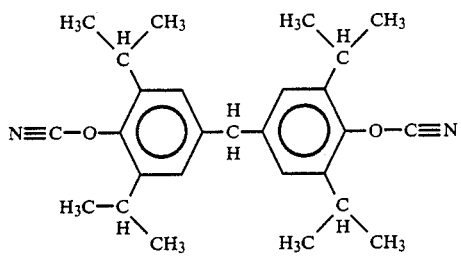

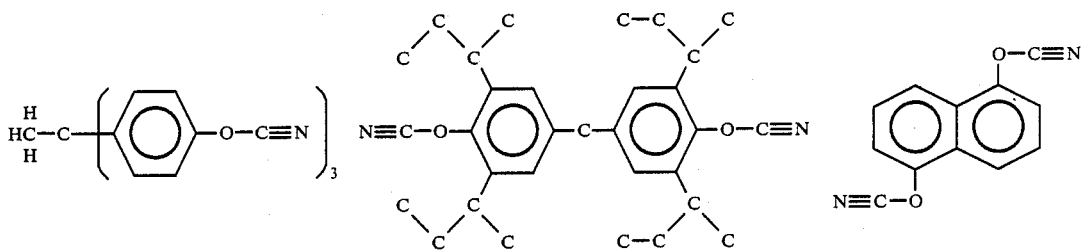

As can be seen, virtually any aromatic moiety, which meets acceptable solubility and reactivity conditions, can be employed as R, provided it has sufficient aromatic character. The aromatic rings R can be substituted or unsubstituted. This substitution should be controlled to avoid solubilities that are too high, thus preserving "out time." As shown, substitution can be in virtually any position, and the molecular weight of the latent catalyst is not limited, except for functional considerations. Hetero atoms, and linkages between aromatic rings, can be used. In general, it is preferred that R be as symmetrical as possible.

These catalysts can be easily prepared by conventional reaction between dicyanates and imidazoles, both commercially available reactants. The reaction follows the scheme forth below.

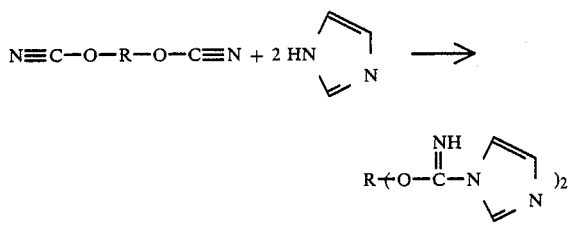

Of course, as indicated, their reaction may be prepared by using stoichiometric amounts. While the reaction will go forward under ambient conditions, application of a modest amount of heat will drive the reaction at a greater rate.

The resultant latent catalysts are compatible with, and easily dispersed in, epoxy resin systems, or epoxy resin prepolymers, of a wide variety, and are not limited to any particular physical state or chemical requirements, save that the resin system must be epoxy based. In general, the amount of latent catalyst present in the system will be dictated by the intended application, and processing speeds and demands. However, a range of 0.1%–20%, by weight, has been identified as acceptable in conjunction with polyglycidyl ether systems, and a particularly preferred range is 1–12%, by weight. Of course, modifications for particular systems, can be made by those of ordinary skill in the art, through routine testing.

The resultant epoxy systems, are easily used, and easily cured, by exposure to relatively low temperature for a period of one hour or less, for conventional cure temperatures and a few days at room temperature. The resins will cure at temperatures ranging from about 50° F. up to about 360° F.

In a particularly preferred embodiment, suited for use as an adhesive in laminates and the like, the resin is used and cured at room temperature (e.g., 70° F.) over a period of a few days. This significant property allows construction of the laminate over time, allows for modification and the like, and completely avoids the need for heating, associated apparatus, and the like.

The invention may be further understood and described with reference to the following examples.

I. PREPARATION OF DICYANATE-IMIDAZOLE

To a solution of 136 parts of imidazole (2.0 moles) in 408 parts of ethyl acetate, 278 parts of bisphenol A dicyanate (1.0 mole; manufactured by Interez, Louisville, Ky.) in 834 parts of ethyl acetate were added slowly. The reaction temperature was maintained at 60°–65° C. during addition. After the addition, the mixture was stirred for another half hour at 60°–65° C. The batch was cooled down to 30°–35° C. and the precipitates were filtered by suction filtration. The white powder was dried under vacuum at 50°–60° C. M.P.=175°–177° C.; actual yield=95–97%.

If the setting (gel time is a few days) at room temperature is desired, a high degree of catalyst (above about 10 pph) must be used. In this embodiment, higher crosslinking resins are also preferred for use. Time examples of more conventional embodiments are set forth below. These examples also demonstrate the excellent shelf life exhibited by resins within the invention.

The above invention has been broadly described and disclosed, and further clarified with reference to particular examples, including particular chemicals and compounds. These are not to be interpreted as limiting in any sense, and the invention should be construed as broadly as possible in conjunction with the claims appended hereto.

TABLE X

Gel Time and Shelf Life of Various Modified Imidazoles in Bisphenol A Glycidyl Ether Resin (E.G., Epon 828)

| Sample No. | Dicyanate used to Adduct with Imidazole | pph cat.* to Epoxy | Gel Time (min) 200 F | 250 F | 300 F | Shelf Life R.T. (days) |
|---|---|---|---|---|---|---|
| 1 | Tris-(cyanatophenyl) ethane | 4.5 | 25 | 4 | 1.5 | 30 |
| 2 | Dicyanato diphenyl sulfide | 4.3 | 38 | 5 | 2 | 56 |
| 3 | Bisphenol A Dicyanate | 4.8 | 24.5 | 3 | 1.5 | 21 |
| 4 | Tetramethyl dicyanatophenyl methane | 5.1 | 29 | 4.5 | 1.6 | 20 |
| 5 | 1,5-Dicyanato naphthalene | 4.0 | 48 | 5.5 | 2 | 58 |

*The pph of catalyst used was adjusted in each formulation so that there was equal amount of imidazole in all the systems.

What is claimed as new and desired to be secured by Letters Patent of the United States is:

1. A latent epoxy resin catalyst, of the formula

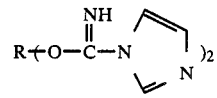

wherein R is aromatic or aralkyl and may contain hetero atoms, and is further characterized as being limited, in molecular weight, such that the catalyst is physically compatible with epoxy resin systems.

2. The catalyst of claim 1, wherein R is selected so as to balance solubility of the catalyst in a preselected epoxy resin.

3. The catalyst of claim 1, wherein 1 or more of the carbons of the imidazole ring of Formula I is substituted with a lower alkyl or aryl of $C_{1-12}$ halo or nitro.

4. A one-component epoxy resin system, comprising:
an epoxy resin prepolymer, and
the latent catalyst of claim 1, dispersed throughout said prepolymer.

5. A one-component epoxy resin system, comprising:
an epoxy resin prepolymer, and
the latent catalyst of claim 2 dispersed throughout said prepolymer.

6. The catalyst system of claim 4, wherein said catalyst is presented in amounts of 0.1–20%, by weight.

7. The epoxy resin system of claim 6, wherein said catalyst is present in amounts of 1–12%, by weight.

8. The one-component epoxy resin system of claim 4, wherein said epoxy resin is based on a polyglycidyl ether.

9. An article of manufacture, comprised of a cured epoxy resin, said epoxy resin being formed by exposing the article containing an amount of uncured epoxy resin system of claim 4 to temperatures of at least room temperature for a time sufficient to cure said resin.

* * * * *